United States Patent [19]

Conway

[11] Patent Number: 5,217,608

[45] Date of Patent: Jun. 8, 1993

[54] MULTI-COLUMN PLANET CENTRIFUGE CHROMATOGRAPH

[75] Inventor: Walter D. Conway, Williamsville, N.Y.

[73] Assignee: The Research Foundation of State University of New York, Albany, N.Y.

[21] Appl. No.: 659,847

[22] Filed: Feb. 22, 1991

Related U.S. Application Data

[63] Continuation-in-part of Ser. No. 223,024, Jul. 21, 1988, abandoned.

[51] Int. Cl.$^5$ ............................................. B01D 15/08
[52] U.S. Cl. .................................. 210/198.2; 210/657
[58] Field of Search .............. 210/635, 656, 657, 658, 210/198.2; 55/386; 422/70

[56] References Cited

U.S. PATENT DOCUMENTS

| | | | |
|---|---|---|---|
| 4,228,950 | 10/1980 | Ito | 210/672 |
| 4,321,138 | 3/1982 | Ito | 210/657 |
| 4,324,661 | 4/1982 | Ito | 210/657 |
| 4,414,108 | 11/1983 | Ito | 210/198.2 |
| 4,430,216 | 2/1984 | Ito | 210/198.2 |
| 4,484,061 | 11/1984 | Zelinka et al. | 219/301 |
| 4,487,693 | 12/1984 | Ito | 210/657 |
| 4,532,039 | 7/1985 | Ito | 210/198.2 |
| 4,554,436 | 11/1985 | Chlosta et al. | 219/385 |
| 4,594,500 | 6/1986 | Wright | 219/296 |
| 4,615,805 | 10/1986 | Ito | 210/657 |
| 4,714,554 | 12/1987 | Ito | 210/198.2 |
| 4,726,822 | 2/1988 | Cates | 210/198.2 |
| 4,753,734 | 6/1988 | Ito | 210/198.2 |
| 4,792,395 | 12/1988 | Lee | 210/657 |
| 5,024,758 | 6/1991 | Ito | 210/198.2 |

OTHER PUBLICATIONS

Mandaya et al., Countercurrent Chromatography, Marcel Dekker, Inc., 1988, pp. 601-603.
Ito, Y. et al., J. of Chromatography, 301 (1984) 405-414.
Romanach, R. J. et al., J. Liquid Chromatography, 11(1); 91-105 (1988).
Knight, M. et al., J. Liquid Chromatography, 8(12), 2281-2291 (1985).
Ito and Conway, Journal of Chromatography, 301 (1984) pp. 405-414.
Ito, Y., Journal of Chromatography, 214, (1981) pp. 122-125.
Ito, Y. Journal of Chromatography, 188 (1980) pp. 43-60.
Ito, Y. et al., Journal of Chromatography, 475 (1989) pp. 219-227.

Primary Examiner—Ernest G. Therkorn
Attorney, Agent, or Firm—Howard M. Ellis

[57] ABSTRACT

A multi-column countercurrent chromatograph utilizes a single reel with a plurality of columns, typically preparative, semi-preparative and analytical types helically wound around a common central axis in various combinations. The multi-coil column may consist of an inner preparative coil in the range of 215 ml; a 75 ml semi-preparative intermediate coil and 15 ml mini analytical coil for rotation around a central axis. The mini coil is particularly useful for preliminary tests of solvent systems or for separations on a few milligrams of sample. The intermediate coil is useful for preparative separations of larger samples in less than an hour. By connecting the intermediate and larger coils in a series arrangement the resolution obtained will be double that achieved with the intermediate coil alone. Separations can be repeatedly injected without loss of the stationary phase. Individual coils may be used without the need for rebalancing the instrument.

19 Claims, 9 Drawing Sheets

MULTI-COLUMN PLANET CENTRIFUGE CHROMATOGRAPH

This invention was made with Government support under SBIR Grant No. R44-RR03167-03, awarded by NCI, NIH. The Government may have certain rights in this invention.

CROSS REFERENCE TO RELATED APPLICATION

This application is a continuation-in-part of Ser. No. 07/223,024, filed Jul. 21, 1988, now abandoned.

BACKGROUND OF THE INVENTION

This invention relates to improved countercurrent chromatography systems and more particularly to multi-column planet centrifuge type countercurrent chromatography systems.

Countercurrent chromatography is the generic designation for a family of liquid-liquid partition methods that do not employ a solid supporting matrix. Thus, countercurrent chromatography offers advantages over other chromatographic methods in that it is free from all complications arising from the use of solid supports, such as excessive adsorptive loss and denaturation of samples, contamination, tailing of solute peaks, etc. However, historically the challenge for countercurrent chromatography has been to achieve partition efficiencies that are comparable to methods which rely upon solid supports.

A countercurrent chromatograph (CCC) is a device which employs two liquid phases wherein one phase is held stationary in a column (usually a coil of tubing) by gravitational or centrifugal means, while a second immiscible liquid is passed through the first. Components of a sample introduced in the stream (usually injected in a small volume) are separated according to their partition coefficients. Partition coefficients are defined herein as the ratio of solute concentration in the stationary phase to the mobile phase. Within the generic class of CCCs, is a group of CCCs referred to as Coil-Planet Centrifuges. These have the common characteristic that the stationary phase of the solvent pair is retained in the column by centrifugal means as the column revolves rapidly about a central axis. Highly efficient mixing is then achieved by further rotating the column about its own axis in a planetary motion. As a sample solution is introduced into the column, the solutes will migrate through the column at different rates according to their partition coefficients, all within the pulsating centrifugal force field. The column's coil may be wound in a "multi-layer" configuration which creates gradients within the centrifugal force field that allow faster flow rates and larger volumes of the stationary phase to be retained in the column. This type is referred to as a Multilayer Coil-Planet Centrifuge. An example of this type of CCC is disclosed in U.S. Pat. No. 4,430,216 to Ito which is hereby incorporated by reference. Another type of CCC is a "Horizontal Flow-Through Coil-Planet Centrifuge." This differs from a Multilayer Coil-Planet Centrifuge in that the Horizontal Flow-Through Coil-Planet Centrifuge employs eccentrically mounted columns. An example of this type is disclosed in U.S. Pat. No. 4,228,950 to Ito, which is incorporated by reference. These CCCs can both decrease separation time and increase resolution relative to the performance achieved in earlier art.

Techniques of chromatography may be broadly divided into preparative and analytical applications. Preparative methods relate to the purification of mixtures so as to isolate a visible amount of one or more components of the original mixture. The meaning of a visible quantity depends to some extent on the nature of the separation problem and the attitude of the individual practitioner, but generally ranges from a milligram to a gram or even larger quantities. Typically, preparative chromatography is employed in those instances where a quantity of purified substance is required for further study. Isolation of substances in the several milligram range is sometimes referred to as semi-preparative chromatography.

In analytical chromatography, the components of a mixture are simply detected in the effluent stream of a chromatograph by a suitable monitor, such as a uv light absorbing detector. The effluent is discarded with no attempt being made to save the fractions containing the isolated components. The separation is usually recorded as a graph of detector response versus effluent volume, or alternatively simply as time since flow rate is usually constant, i.e. a chromatogram. The chromatogram indicates the number of detectable components in a mixture and provides information on their chromatographic properties.

In CCC, preparative columns or coils are typically 300 ml or larger in volume while analytical columns are usually 30 ml or less. Both types are usually made of tubing with internal diameters of at least 1.6 mm for preparative columns whereas analytical columns usually have inside diameters of less than 1.07 mm.

The multi-layer type coil planet centrifuge is presently one of the most efficient CCCs in terms of good sample capacity, typically 1 gram for a 300 ml column, good resolution (separation) of sample components and fast separation times. However, to perform both preparative and analytical separations the options are either purchasing separate devices at considerable expense, or alternatively, utilizing a convertible type CCC. Multilayer coil planet centrifuges are available in the preparative and analytical range, and they allow columns to be changed so as to accommodate a range of samples with the same instrument. However, they require the time consuming task of rebalancing since separation columns of different size vary appreciably in weight.

Countercurrent chromatography is still primarily a preparative system for purification of samples of about one gram. CCC systems have the added disadvantage of requiring several hours to run and do not offer the convenience of smaller analytical columns which permit characterizations of solvent systems in a matter of minutes.

In U.S. Pat. No. 4,228,950, Ito teaches that two columns can be placed in a coil planet centrifuge on separate axes as shown in his FIG. 1. The flow tubes from these columns can be led independently to the apparatus exterior, where they can be connected together to increase column capacity, as shown in his FIG. 3 and FIG. 5B. However, it should be noted that these columns each operate in a different manner and are subject to quite different force fields.

Column II in his FIG. 1 undergoes what may be called a "Ferris Wheel" motion. Analogous to the car in a Ferris Wheel, the column holder does not rotate on its own axis in the course of its orbit around the central axis. This motion is induced using a stationary solar pulley connected with a belt to a pulley of equal diameter on the column holder. In contrast, column I in his FIG. 1 undergoes a tumbling car motion, in which the Ferris Wheel car would be tumbled forward twice in the course of each orbit around the central axis. This is induced by using a stationary sun gear coupled to a gear of equal diameter attached to the column holder.

I have found that columns eccentrically mounted so they do not rotate on the axis they are mounted on are less conducive to stationary phase retention and exhibit generally poor separations.

Accordingly, it would be highly desirable to have an efficient and economical means for conducting countercurrent chromatography with a multiplicity of columns wound on a single axis which can provide both analytical and preparative capability with high resolution.

SUMMARY OF THE INVENTION

It is a principal object of the present invention to provide for a coil planet centrifuge chromatograph. The apparatus comprises separation column means, support means for the separation column means, and first and second spaced, parallel axes normal to the plane of the support means. The support means is centrally mounted for rotation about the first axis. The separation column means is eccentrically mounted on the support means for rotation about the second axis. Means are provided for revolving the support means and the separation column means around the first axis while simultaneously rotating the separation column means around the second axis. Counterweight means are employed for balanced rotational movement of the apparatus. The separation column means comprises single reel means having a central axis and two or more mutually exclusive separation coils adjacent to one another and helically wound around the central axis of the single reel means to form a multi-layered coil. The separation coils of the separation column may include preparative, semi-preparative and analytical types in various combinations.

Accordingly an overall object of the invention is to provide for an improved CCC in which a multiplicity of separation columns are wound around on a single, common axis which can provide both preparative and analytical capability.

The invention also contemplates embodiments in which at least one preparative type column is helically wound on the single reel closest to the central axis of the reel and an analytical coil comprising at least one helically wound layer of tubing is wound concentrically over the preparative coil. This smaller outer analytical column can permit characterization of solvent systems in about 15 minutes, thereby facilitating the optimization of the solvent composition.

It is yet a further object of the invention to provide for an improved CCC having a novel multi-column, multi-layered separation coil helically wound on a single spool. Two or more separation coils are positioned adjacent to one another and wound around the same central axis. The invention contemplates flow lines from each of the coils lead via an anti-twisting mechanism of known design to the exterior of the instrument, permitting the choice of either coil without the need to disassemble the instrument and mount an individual column. In addition, semi-preparative and preparative columns may be connected in series to increase the resolving capabilities of the system.

It is yet a further object of the invention to provide a CCC apparatus having the improved features described hereinabove wherein the separation column is located in an interior chamber and includes means for warming a dynamic solvent to and maintaining the dynamic solvent at a desired temperature prior to entry of the dynamic solvent into the separation column. Thus, a more particular object is to provide an improved temperature controlled CCC system which will decrease separation time and achieve partition efficiencies which are comparable to systems relying on solid supports.

These and further features, objects and advantages of the invention will become apparent to those skilled in the art from the following detailed description and appended drawings.

BRIEF DESCRIPTION OF THE DRAWINGS

For a further understanding of the invention as well as its characterizing features, reference should now be made to the following detailed description thereof taken in conjunction with the accompanying drawings, wherein.

DETAILED DESCRIPTION OF THE INVENTION

Figure 1:
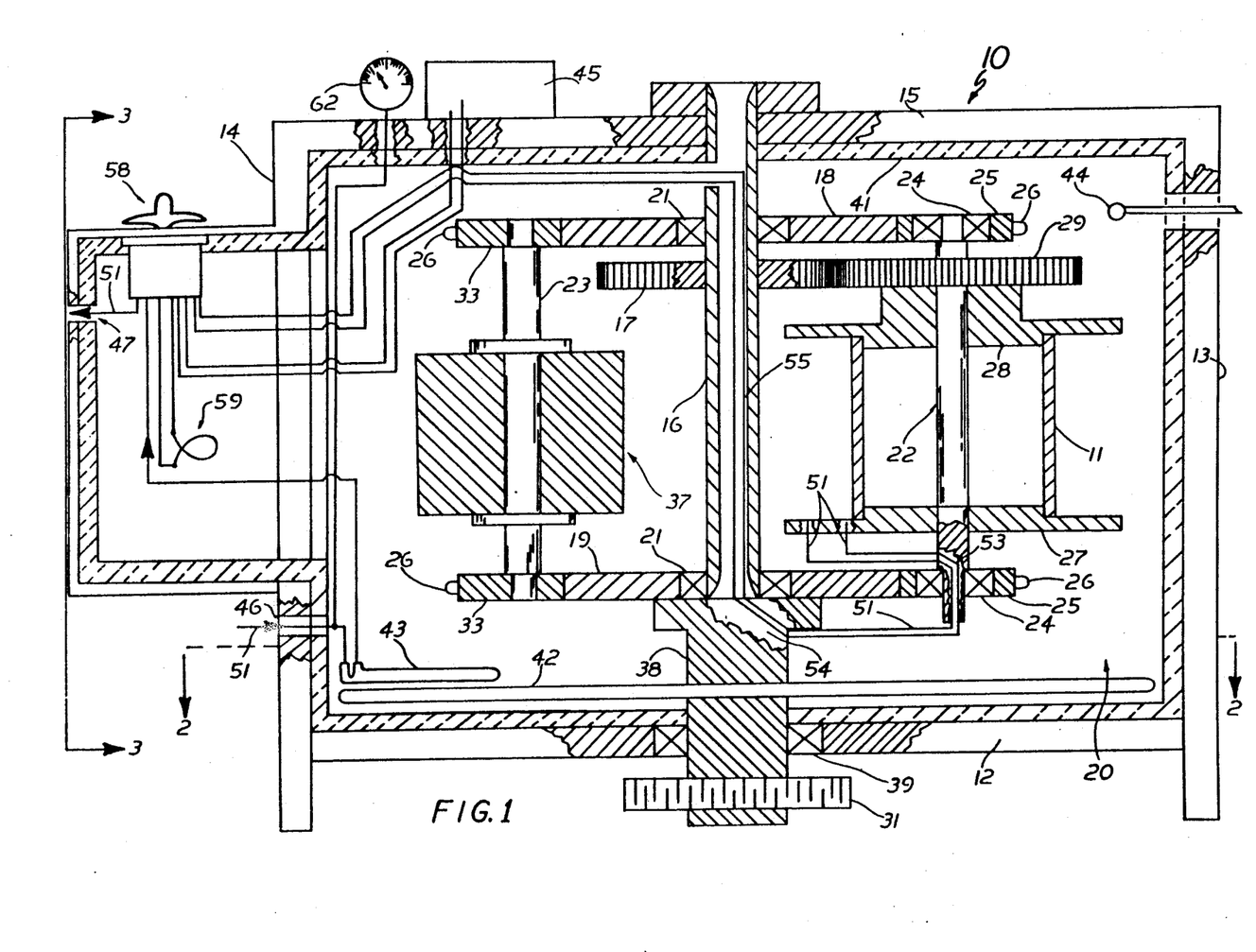
FIG. 1 is a detailed cross-sectional view, partly in elevation, taken through an improved countercurrent chromatograph in accordance with the present invention.

An improved countercurrent chromatograph is schematically illustrated in FIG. 1, where 10 generally designates a typical design of an improved countercurrent chromatograph with a separation column reel or other cylindrical surface 11 shown without separation coils. The separation column reel 11 may be adapted to hold at least one separation column, as will be discussed in greater detail below. The assembly 10 is supported on a base plate 12 to which are rigidly secured opposite parallel vertical upstanding wall members 13, 14, rigidly connected by a top plate 15. A vertical central stationary shaft 16 is rigidly secured to and extends through top plate 15. A sun gear 17 is rigidly secured on shaft 16. A pair of spaced parallel support plates 18, 19 are perpendicularly journalled on central stationary shaft 16 by means of bearings 21. Planetary shaft 22 is journalled between the outer portions of support plates 18 and 19 by means of bearings 24, retentively engaged by detachable bearing blocks 25 secured to the ends of the support plates by means of fastening screws 26. Secured on planetary shaft 22 is the separation column reel 11 having a lower column end plate or flange 27 and an upper column end plate or flange 28. Rigidly secured to the upper column end plate 28 of separation column reel 11 is a planetary gear 29 identical to stationary sun gear 17 and meshingly engaged therewith.

Vertical shaft 23 is retentively engaged by detachable bearing blocks 33 secured to the ends of the support plates 18 and 19 by means of fastening screws 26. A counter weight 37 is mounted on vertical shaft 23 opposite separation column retaining means 11. For mechanical stability, the midportion of support plate 19 is rigidly connected to a short coupling pipe 38 which is supportingly journalled in base plate 12 by means of a bearing 39.

A toothed drive pulley 31 is mounted on the lower portion of base plate 12 and is connected by a belt (not shown) to a motor (not shown).

For embodiments employing means for warming a dynamic solvent the inside of all exterior surfaces including base plate 12, top plate 15 and wall members 13 and 14 there is provided insulating material 41. This material must be solvent resistant and stable at operating temperatures. An example of an acceptable insulating material for many purposes is foamed polyethylene, one brand of which is Ethafoam ® owned by Dow Chemical Company of Midland, Mich.

Figure 2:
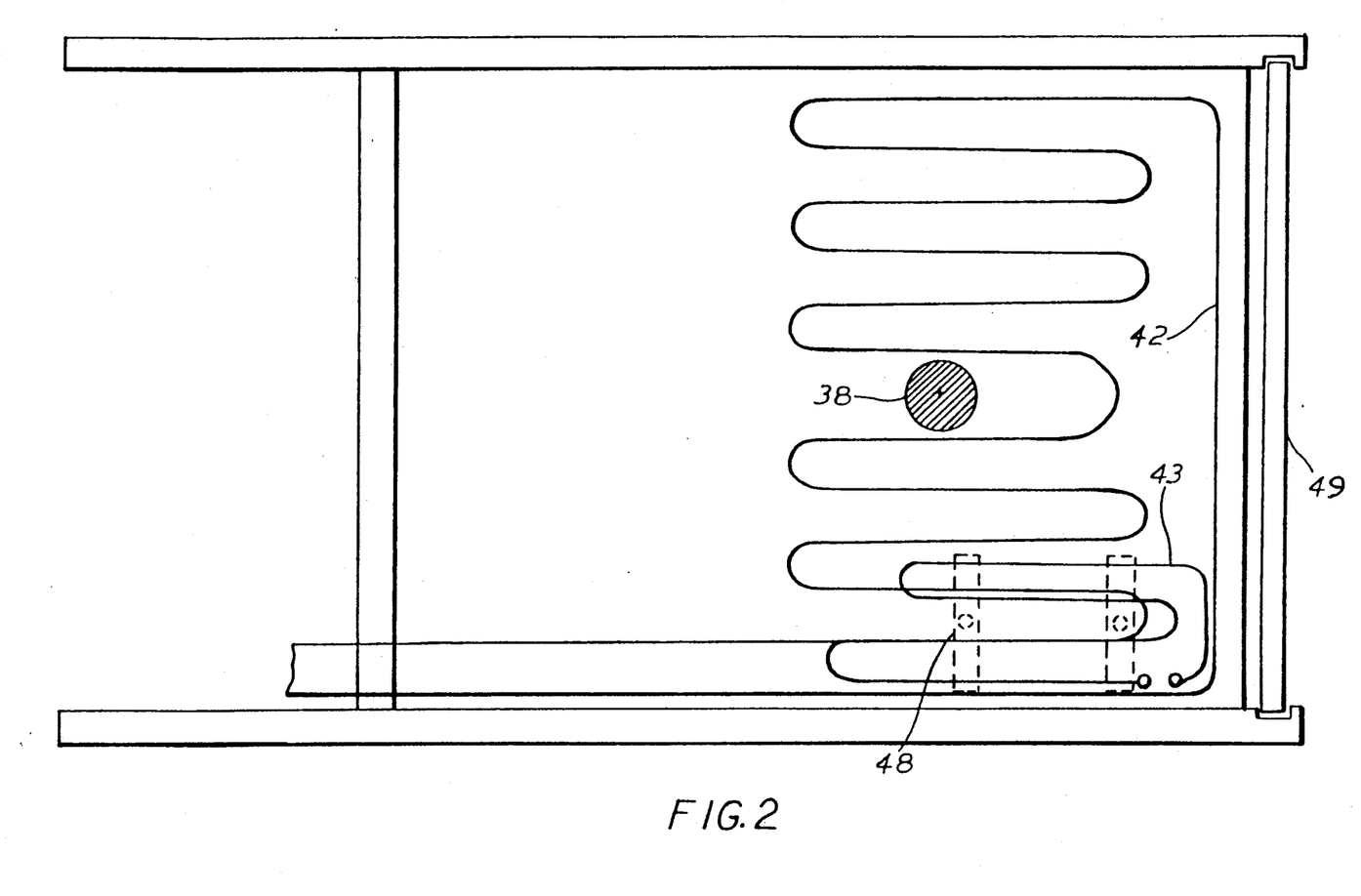
FIG. 2 is a horizontal section on the line 2—2 of FIG. 1 and in the direction of the arrows, showing a heating unit and warming tube.

A warming means comprising a heating unit 42 and a warming tube 43 can be seen in FIG. 1. The heating unit 42 is located such that a desired temperature may be reached within the chamber 20. The heating unit 42 should be a heater sufficient to heat the interior chamber up to as much as 100° C. Although a preferred range may be between about 40° C. to about 60° C. The temperature should be sufficient to increase the resolution and decrease the separation time of separations utilizing a variety of solvent systems, including viscous solvent systems such as 2-butanol, with retention of larger volumes of the viscous phase. A preferred type may be a metal sheathed Glasrope heater. An example may be a serpentine aluminum or stainless steel sheathed Glasrope heater (as can be seen in FIG. 2) giving a total of 100 watts. A commercially available brand by Hotwatt Inc., Danvers, Mass. may be utilized. It is preferable that no electrical connections or electrical switches are placed within the chamber for reasons of safety since flammable solvents may be employed in the column. However, any configuration meeting the objectives of the invention would suffice. Although the heating unit 42 may lie directly on the insulating material 41 at base 12, at temperatures which would soften and create depressions in the insulating material, the top and bottom of the heating assembly may be covered with light gauge sheet metal (aluminum or stainless steel for example) or any other suitable material (not shown in figures). It is also possible to completely enclose the heating unit with a light gauge sheet metal or other suitable material.

A warming tube 43 is placed sufficiently proximate the heating unit 42 such that thermal equilibrium between the dynamic solvent and the desired ambient temperature of the CCC may be achieved. "Dynamic solvent" as used herein is intended to mean that the solvent is continuously flowing through the solvent warming means as it is being heated. The desired temperature should be reached prior to entry into the separation column and most preferably prior to entry into the valve assembly 58 and maintained until the solvent passes through the separation column. The warming tube 43 may comprise a stainless steel tubing or any other glass-lined or PTFE-lined metal tubing or other suitable materials which have good heat transfer properties, and may be placed directly in contact with the heating unit 42 where air conduction may be insufficient to warm a cooled influent stream within the transit time of a coil of predetermined length. This unique dynamic solvent warming means warms the solvent to the desired temperature while it is in transit, through the warming tube.

In a preferred embodiment, the heating unit 42 includes two 50 watt serpentine coils of aluminum sheathed Glasrope heaters approximately 12 feet in length in total being covered with a light gauge metal sheet and lying on the insulating materials 41 at base 12. Directly in contact with this heating unit is a warming tube 43 made of stainless steel and being about 4 feet long and attached to the heating unit by any suitable attaching means 48, including clamps or holding brackets as shown in FIG. 2. The warming tube 43 may be in the shape of a coil.

The length of the heating unit 42 and the warming tube 43 are of sufficient length for temperature equilibrium to occur prior to entry into the separation column and most preferably prior to entry into the valve assembly. The length of the heating unit and the warming tube may be calibrated by the use of thermistors in the flow line at specific places to measure temperature and ensure that the desired temperature is reached prior to entry into the critical areas. Therefore, a novel dynamic solvent warming means which allows warming of dynamic solvent to the desired temperature as it passes through the warming tube is disclosed.

Figure 3:
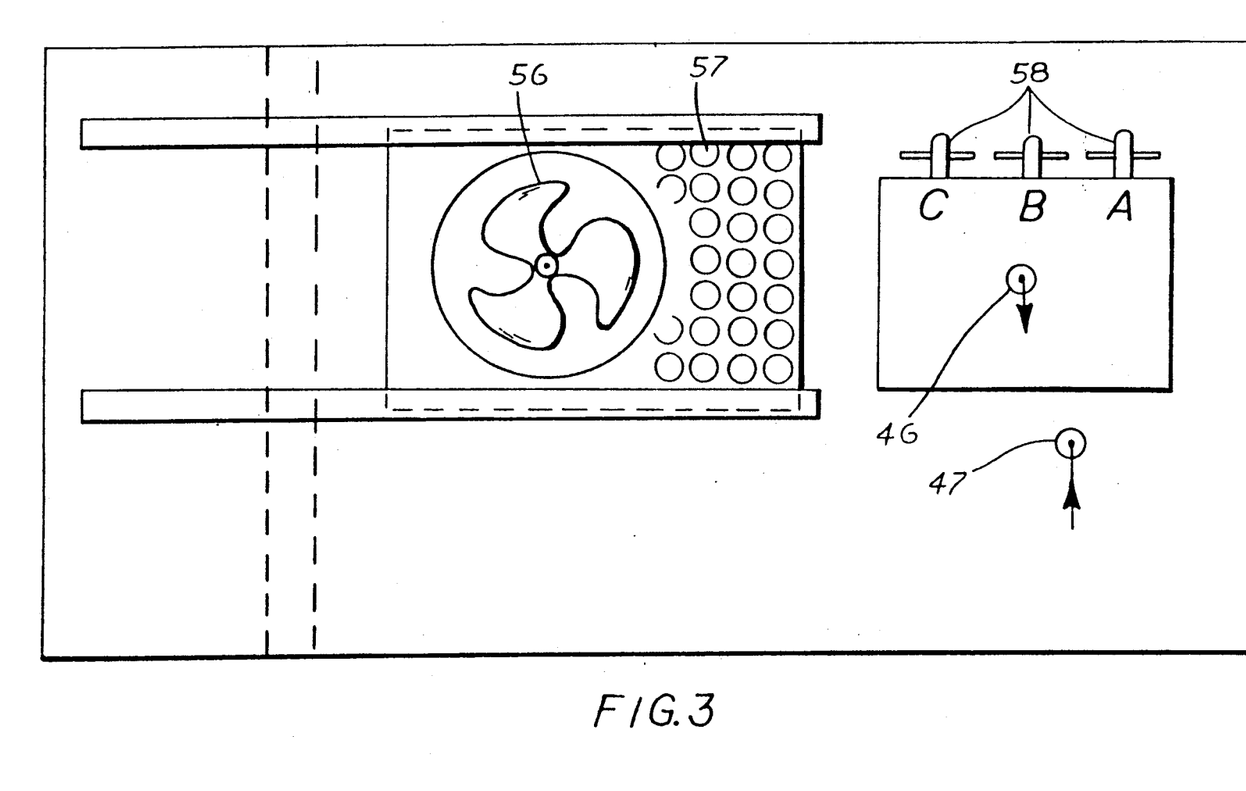
FIG. 3 is a plan view of a side of the countercurrent chromatograph on the line 3—3 of FIG. 1 and in the direction of the arrows.
Figure 4:
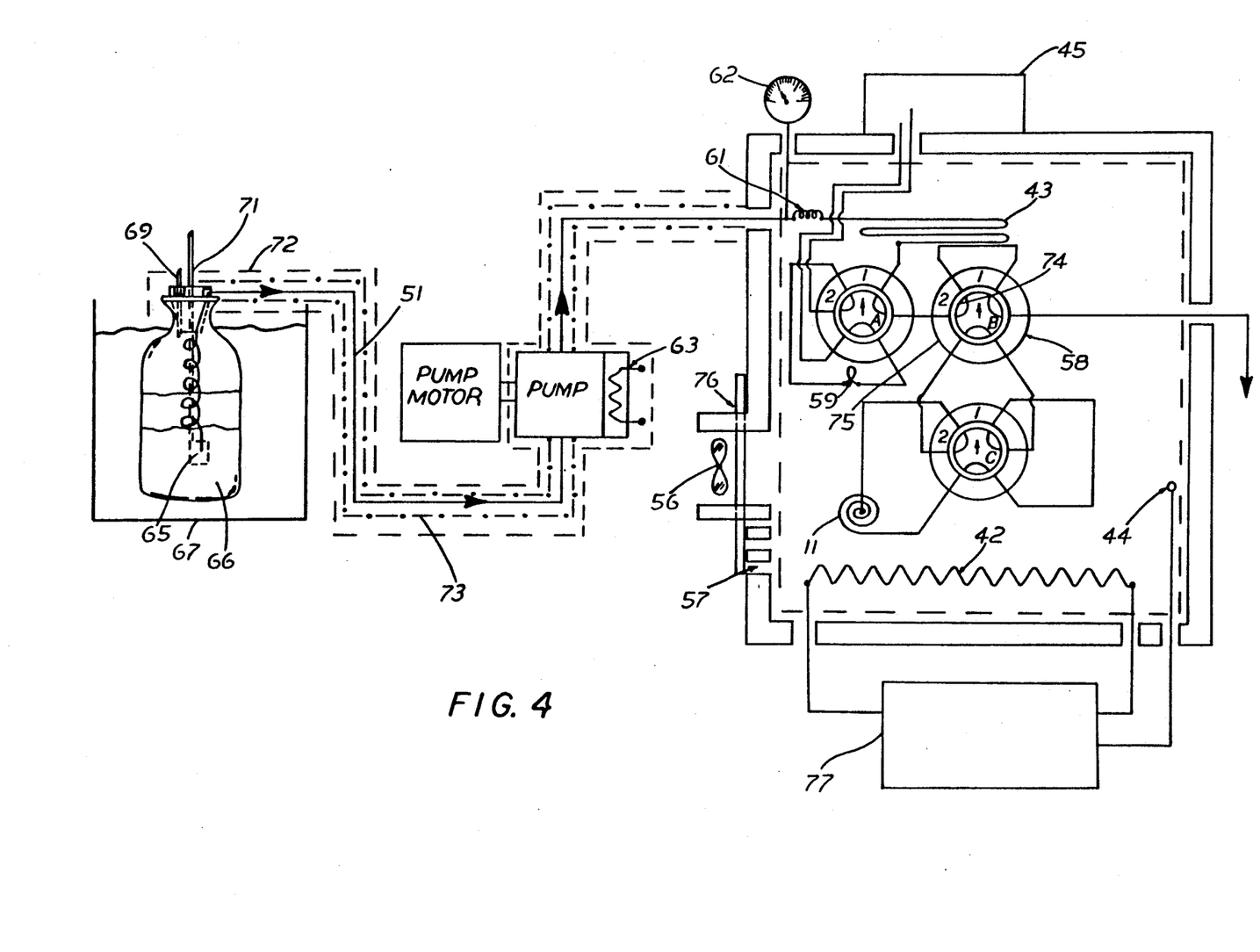
FIG. 4 is a diagrammatic representation illustrating the flow paths of the solvents and sample; the heated and insulated pump; and the insulated and temperature control sheathed flow lines according to the present invention.

The separation column represented in FIG. 1 by reel 11 may be prepared by winding tubing in a helical pattern around the separation column to form a predetermined number of layers. The tubing may be of any suitable materials, e.g., polytetrafluoroethylene (PTFE). The terminals of the column may be connected to flow tubes 51 of the proper diameter. The pair of tubes is first led through a flow tube passageway 53 in shaft 22 and then are passed through a flow through passageway 54 in coupling pipe 38 to enter the bore 55 of the central stationary shaft 16. These flow tubes may be lubricated with grease and preferably are further protected from abrasion damage by employing a surrounding lining of Tygon or any other commercially available materials as known in the art. This protection may be employed at each supporting end portion of the bore of central stationary shaft 16 to prevent direct contact of the flow tubes with metal parts. The flow lines 51 are then fed into a valve assembly 58. The valve assembly may comprise three control valves as shown in FIGS. 3 and 4. These may be commercially available rotary valves, currently obtained from Rheodyne. Any other commercially available valves, including six-way valves, may able be used. As can be seen in FIG. 4, the valves have a valve rotor 74 and a valve body 75. The numbers 1 and 2 on the valves indicate two positions for the valves. The letters A, B and C indicate the different valves. The number of valves is subject to some choice and the arrangement shown is convenient for instrument operation using a single pump. For instance, valve C for reversing flow direction in the column is merely a convenience since the same result can be obtained by simply changing plumbing connections directly. However, having the valve assembly permits changes to be made without disturbing the temperature equilibrium as would occur on opening the instrument access door (shown in FIG. 2 as 49). This access door should also have insulation on the surface facing the chamber 20.

The sample loop 59 is also heated within the chamber 20 by heating unit 42, since injecting a cold sample through sample loading means 45 may disturb the phase equilibrium within the column. An example of a loading means may be a syringe for loading sample by suction. In practice a sample may be warmed exterior to the instrument and drawn into the CCC, or a cold sample may be drawn in and sufficient time allowed for it to warm to instrument temperature in the sample loop 59 before switching a valve to an injection position. The sample loop consists of a length of PTFE (polytetrafluoroethylene, Teflon TM) tubing of sufficient volume to accommodate a particular sample size. This may typically vary from less than 2 ml to as much as 50 ml. The flow lines are kept within the instrument chamber by passing them through a hole in the vertical stationary central shaft 16.

On FIG. 1, 46 and 47 represent influent and effluent ports respectively for the solvents. However, the locations of these ports may be changed to other desired locations not interfering with the operation of the CCC. As best seen in FIGS. 1 and 4, a temperature sensing probe 44 and a pressure gauge 62 may also be included as optional ancillary equipment.

FIG. 3 shows a fan 56 and vent holes 57. The position of the fan and vent holes is arbitrary. They should be positioned such that sufficient cross ventilation is obtained to cool the unit and enable performance at room temperature. The fan may be needed because, in an insulated instrument, friction in the rotating assembly may otherwise raise the interior temperature above a desired temperature. This would interfere with separations intended to be done in the vicinity of room temperature. Some type of closure is necessary to cut off these passageways for operation at elevated temperature. A slideable door 76 is shown in FIG. 4, but other structures such as an interior plug are also possible.

FIG. 4 is a detailed schematic drawing which illustrates the flow patterns. This incorporates ancillary equipment comprising a constant temperature bath 67, phase system reservoir 66 (solvent reservoir), temperature controlled flow lines and a temperature controlled pump 63.

When such a complete system is used, the warming tube may be eliminated, however it may still be utilized to provide final assurance that the incoming solvent is at instrument temperature.

In the device in FIG. 4, the flowline inlet 65 is coiled and can be raised and lowered in the reservoir 66 using an adjustable rod 71, thereby permitting choice of either the upper or lower phase without removing the inlet line from the reservoir. The reservoir may be placed in a heated waterbath 67. Preferably, the waterbath should be of sufficient depth to cover the reservoir to as near the top as possible. In addition, it may be convenient that the reservoir be transparent so that the solvent level and flowline inlet position can be observed. In addition, the rod may be maintained at the desired vertical position by use of a clamp on the rod or by any other means to restrict movement. The reservoir may also have a means for adding or removing solvent 69. FIG. 4 also shows that a temperature readout and temperature controller unit 77 may be attached to the heating means 42 and temperature sensing probe 44.

The flow line 51 in FIG. 4 may be covered by a temperature control sheath 73. The flexible sheath for maintaining constant temperature in flow lines has numerous applications including use with CCCs. In use with CCCs, the sheath may be utilized to heat a flow line above or cool below room temperature. Where it is necessary to heat (or cool) a flow tube from a heated reservoir to an apparatus, the conventional approach is to immerse it in a controlled temperature stream within a rigid or flexible conduit. This requires seals to be made where the flow line enters and exits the controlled temperature stream. These often leak and in any case are inconvenient when it is necessary to remove or modify the enclosed line. The sheath disclosed herein comprises an annular sheath, slotted on the side to permit the flow line to be nestled within the cavity. The tubing can be inserted and removed without leakage of the water in the annular sheath itself.

Figure 5A:
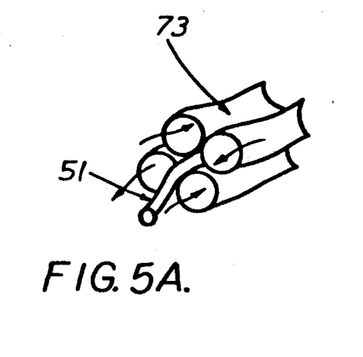
FIGS. 5A-5G are an enlarged view of several embodiments of the temperature control sheathed flow lines.
Figure 5B:
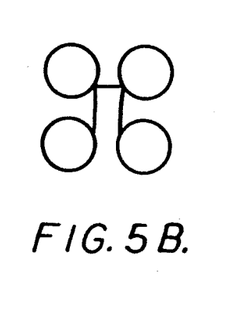
Figure 5C:
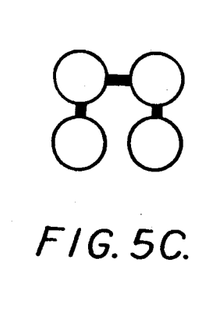
Figure 5D:
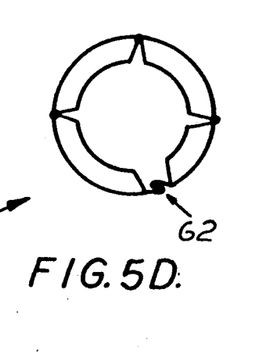
Figure 5E:
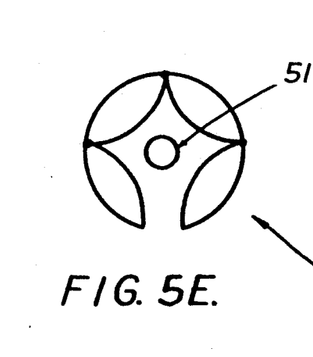
Figure 5F:
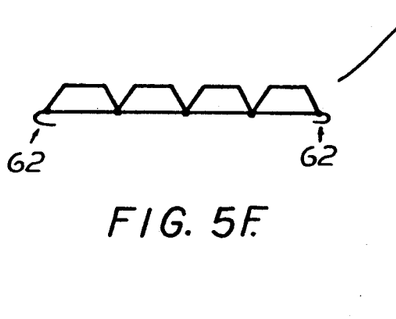
Figure 5G:
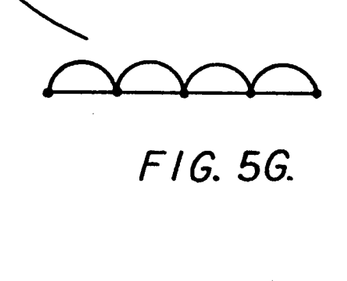

Several embodiments of a suitable sheath are shown in FIGS. 5A-5G. These may be made of standard polyvinyl chloride (PVC) and metal tubing. However, they also may be made by extruding flexible plastic tubing of a specified cross-section. It is preferable to use a tubing which could be cemented or heat sealed such as PVC, silicone or polyurethane. As can be seen in FIGS. 5A and 5E, 51 represents a flow line lying in the temperature controlled cavity formed by the sheath. In FIG. 5A, four tubes 73 through which fluid from a constant temperature bath flows in paths shown by the arrows, can be seen. In this embodiment, the four tubes can be taped together or held together by any other suitable means known in the art. This may then be covered with any type of insulating foam 72 as in FIG. 4. Tubing can also be extruded as 5B and 5C or 5D or 5E. The actual extrusion could be more in the form of 5F or 5G before wrapping around the flowline to form 5D and 5E. A clasping means 62 may also be molded into the extrusion such as can be seen in FIG. 5F to form 5D when folded. This unit could also be covered with insulating foam rubber or plastic tubing.

Figure 6:
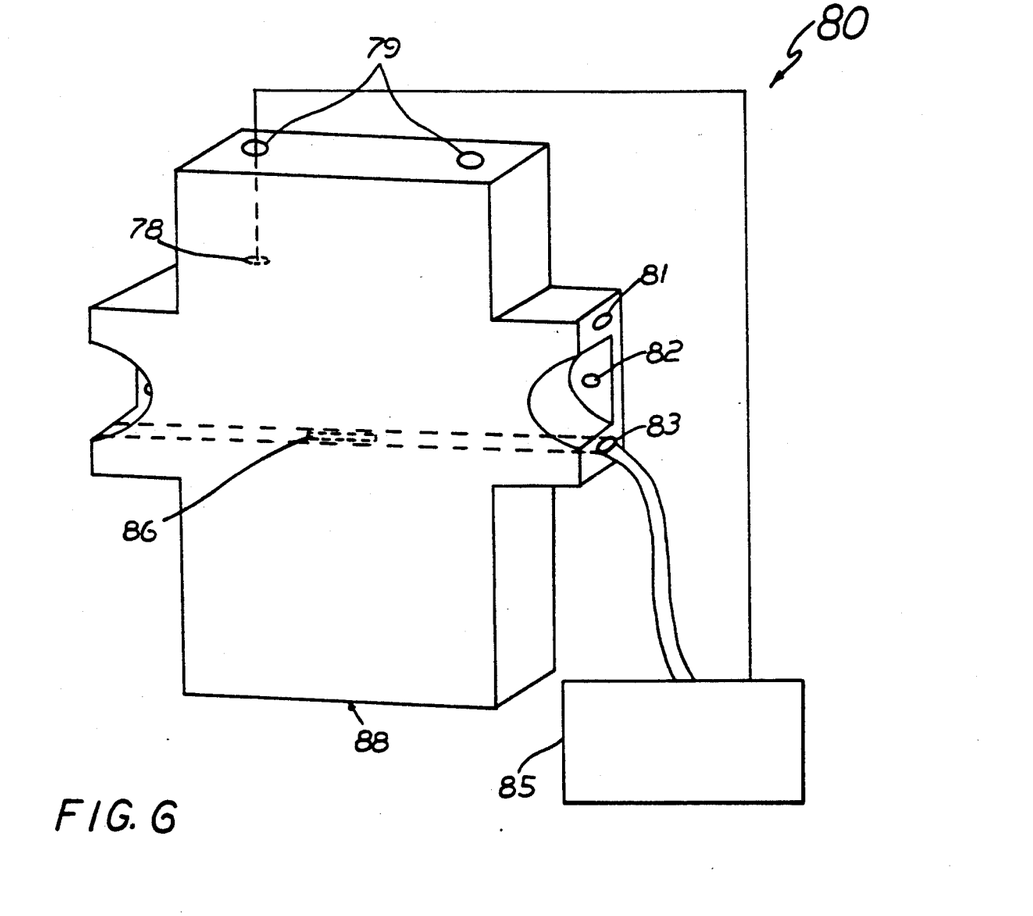
FIG. 6 is a perspective view of the heater for a countercurrent chromatography pump.
Figure 7:
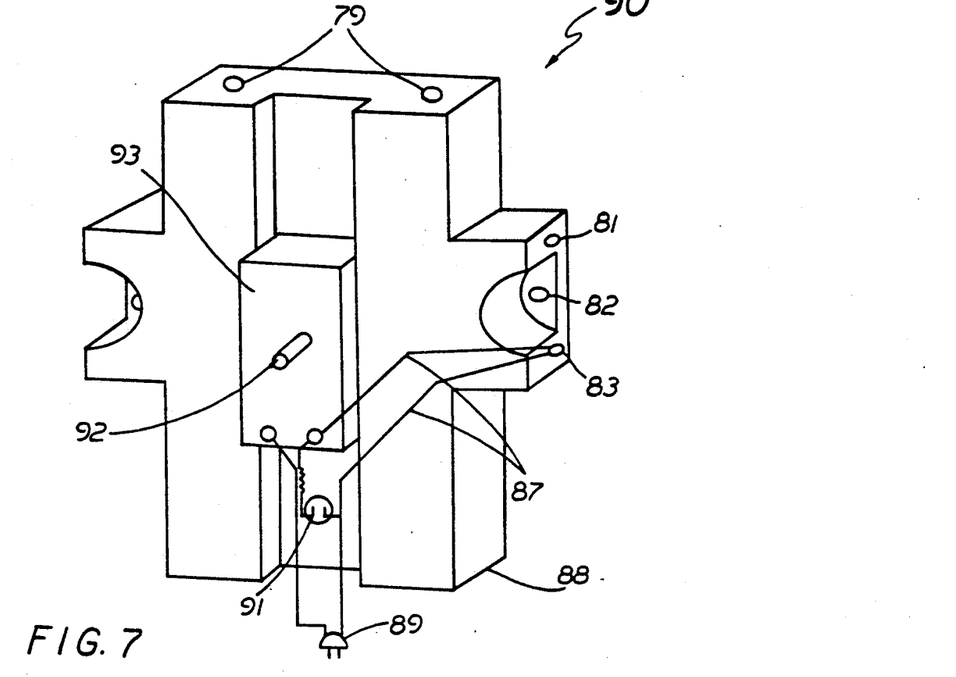
FIG. 7 is a perspective view of another embodiment of a heater for a countercurrent chromatography pump.
Figure 8:
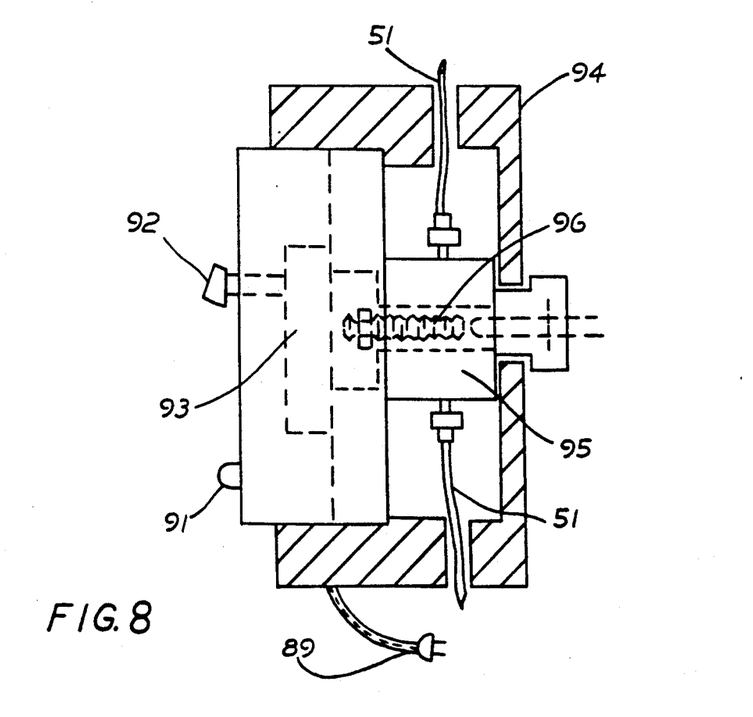
FIG. 8 is a cross-sectional view of the insulated and heated countercurrent chromatography pump.

In addition to the temperature controlled sheath for the flow lines, a heating device 80 may be used with the chromatography pump. The heating means for the chromatography pump is generally designated as 63 in FIG. 4. The heating device consists of an aluminum slab 88 in FIG. 6, heated electrically by an internal cartridge heater 86 (10 watts) in opening 83 for the heater. If additional heat is required another heater may be placed in opening 81. Temperature is regulated by a bimetallic strip adjustable thermoregulator generally designated 85 in FIG. 6 and as 93 in FIG. 7. Other electronic thermoregulator circuits may also be utilized. The device mounts on the pump head of typical high pressure chromatography pumps and is held against the pump head with the screws which normally attach the pump head itself through 82 a hole to pass the pump head mounting screw. Device 80 can be regulated from about 25° C. to over 65° C. The device in accordance with the above provides an efficient means to maintain a desired temperature upon passage through the pump. The device does not heat associated pump parts therefore less time and energy is utilized when compared with heating the entire pump. Wells 79 for temperature measurement are also provided. A temperature sensor 78 as best seen in FIG. 6 may be placed in one of the wells 79. FIG. 7 is another embodiment 90 of a heater for the pump where 87 is the electrical wiring, 92 a temperature control knob, 91 a neon indicator light and 89 an electrical plug. FIG. 8 shows the embodiment of FIG. 7 with insulation 94 and shows the pump head 95 attached with pump head mounting screw 96. As can be seen from FIG. 8, the flow tubes 51 extend from the heated pump head.

Figure 9:
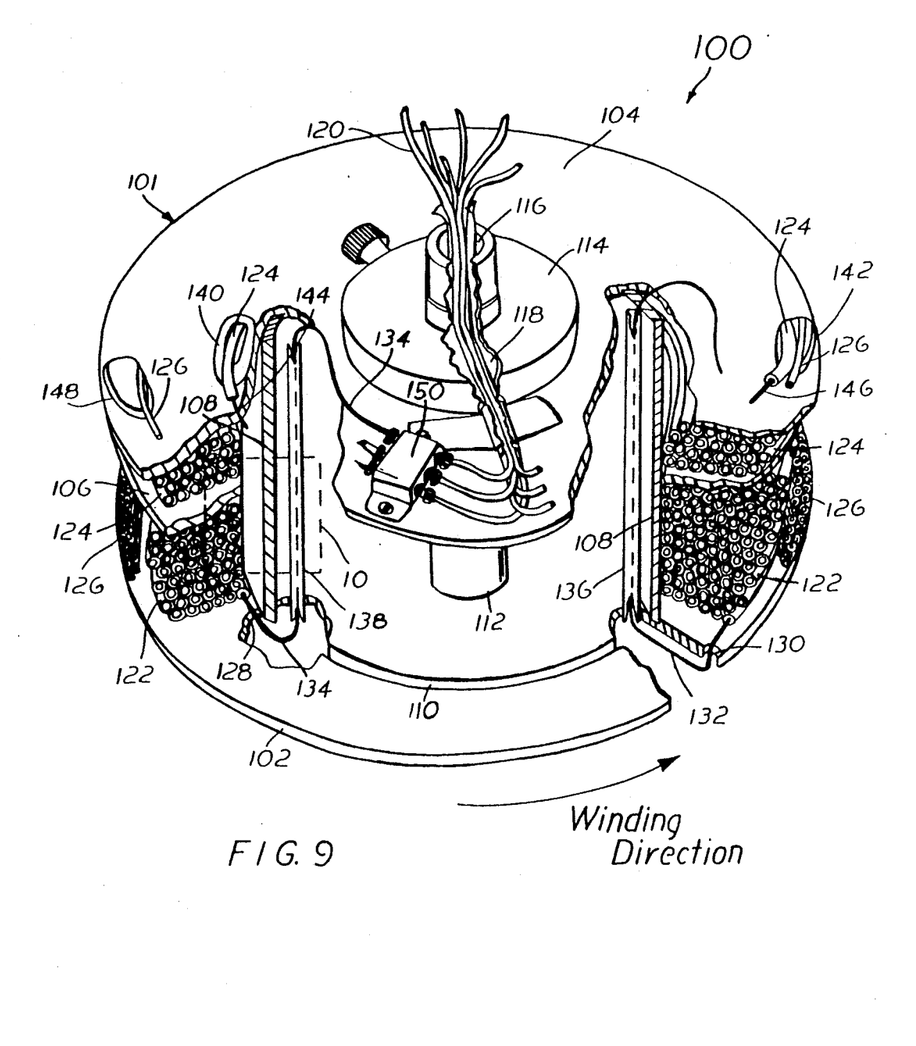
FIG. 9 is a perspective bottom side up view of reel 11 (FIG. 1) with portions removed to show the multi-column, multi-layered chromatographic coils.

FIG. 9 is a detailed view of chromatographic separation column 100 with the column reel 11 of FIG. 1 except the reel has a plurality of different size tubular columns wound thereon and is shown bottom side-up to best illustrate winding patterns and bottom connections for the multi-column CCC coil. In this regard, it has been found conceptually, for instance that both a smaller, i.e. "quarter size" semi-preparative column and one or more multi-layer preparative coils and an analytical coil can be mounted adjacent to one another on the same axis. Generally, flow lines from each can be conveniently conducted through the hub of the reel and inlet and outlet ends of each column, for example, lead to the instrument exterior where they can be connected to peripheral equipment.

All columns on the reel can be used simultaneously, but more frequently only one is utilized at a time and the others filled with water and the flowline ends capped to maintain a balanced system. However, for preparative separations where greater resolution is required than provided by either column alone, both columns, i.e. preparative and semi-preparative, may be connected together in series, which for purposes of this invention is intended to mean connecting the trailing/outlet end of one column to the leading/inlet end of the other column. This benefit is less likely to accrue from series connection of multiple analytical coils because the extra coil dead volume is relatively large compared to the coil volume, whereas the preparative coils have a large volume relative to the flowlines.

One important advantage of the multi-column, multi-layered CCC coil 100 is that a small coil radially wound on the surface of a preparative coil can be used to conduct preliminary investigations of solvent systems in a fraction of the time required for separations on the preparative column, e.g. 15 minutes.

Multi-column coil 100 comprises a reel or spool 101 comprising first and second flanges 102 and 104, respectively. An optional third reel flange 106 positioned between the first and second flanges may be included as a convenience to aid in winding adjacent preparative type tubings. However in the embodiment shown according to FIG. 9, the diameter of flange 106 is somewhat smaller than that of flanges 102 and 104 to allow space for analytical coil windings. The first and second flanges are spaced from one another by a tubular hub 108 which engages with annular groove 110 on the inside surface of the first and second flanges. Dimensionally, hub 110 is approximately one-half the radius of the first and second flanges. An axial reel shaft 112 and a coupling flange 114 are rigidly engaged with the reel for rotational movement. Shaft 112 is in the form of a tubular body having a central opening 116. Coupling flange 114 has a radial opening 118 leading to opening 116 of shaft 112 for receiving all end portions of the tubular columns wound on the reel, as represented by single end portion 120.

The preferred embodiment of the multi-layered CCC column of FIG. 9 is shown with three different helically wound columns; preparative column 122; semi-preparative column 124 and analytical column 126. Preparative column 122 and semi-preparative column 124 are helically wound on adjacent sections of the reel without overlapping with one another. Both are preferably wound on hub 108 closest to the central axis of the reel. Analytical column 126 can then be helically wound around at least one of the inner preparative columns. However, in the embodiment of FIG. 9, the outer analytical column 126 is wound over both the preparative and semi-preparative columns. The important point of this type of arrangement from a performance aspect is that retention of the phases, and particularly the $S_F$ (stationary phase) has been found to be much improved by this multi-layered, multi-column arrangement where all columns are concentrically wound around a common axis rather than having the various columns eccentrically mounted relative to the central axis. This aspect will be discussed in greater detail below.

As previously mentioned the tubing for the columns may be formed of any suitable inert materials, such as PTFE. For purposes of this invention a preparative column is intended to denote tubular coils generally having a length of >35 meters and an i.d. ranging from about 1.3 to about 3.0 mm. A semi-preparative column is intended to mean columns of approximately the same id. as that of preparative coils, but generally shorter in length, i.e. <35 meters. Analytical columns are intended to include tubes having lengths ranging from about 10 to about 50 meters, and more specifically, from about 10 to about 25 meters, and i.ds. of about 0.5 to about 1.3 mm. In combining a small volume analytical column with a preparative column, for instance, the preparative column could typically be constructed of PTFE tubing of 1.6 or 2.6 mm i.d. and a length sufficient to provide a volume of 300 to 400 ml. An analytical column wound on the cylindrical surface of the preparative column could then be constructed of PTFE tubing having an i.d. of 1.0 mm and 15 meters in length which would provide a volume of about 12 ml. The analytical winding would typically consist of a single layer of tubing wound over the preparative column, although for some applications a few layers may be desirable.

While FIG. 9 is illustrative of a column assembly in which the volume of the semi-preparative coil 124 is less than that of preparative coil 122, the present invention also contemplates embodiments in which the volumes of the preparative and semi-preparative columns are substantially the same. Notwithstanding, a multi-column coil like that of FIG. 9 in which the preparative column is three times longer than the semi-preparative column and the i.ds. are equal has been found to be especially advantageous in view of the fact in chromatography that in order to double the resolution of two substances the column length must be increased fourfold. Thus, by connecting the preparative and semi-preparative columns in series, i.e. end-to-end, the combined length of the two columns is four times that of the semi-preparative coil. Under such circumstances, the resolution obtained with the semi-preparative coil can be doubled over this column, if used alone.

In fabricating the column of FIG. 9 preparative coil 122 is helically wound around hub 108. When an even number of radial layers are employed, winding may begin adjacent to opening 128 in the first flange 102 and may end adjacent to opening 130 also in the flange 102. Connector tubes 132 and 134 of a smaller diameter are affixed to the terminal ends of column 122 and are brought to the second outer flange 104 through protective tubes 136 and 138 located inside the reel hub to avoid potential abrasion damage.

Semi-preparative coil 124 can then be wound on the reel between flanges 104 and 106. For an even number of radial layers the winding may begin adjacent to opening 140. The other end of the coil would then be adjacent to opening 142 in flange 104. Openings 140 and 142 are generally oval shaped and appropriately beveled to avoid abrasion damage. The terminal ends of column 124 may also be equipped with smaller protective tubes 144 and 146.

Analytical column 126 is then helically wound over columns 122 and 124. Radial layers may begin at beveled opening 148 and end at opening 142.

The inlet and outlet ends of each of the columns as represented by lines 134 and 132 adjacent to reel flange 104 are joined by connectors 150 (only one shown) positioned adjacent to one another. Connectors 150 serve as a convenient junction means for gathering all six ends of the triple column CCC coil for conducting through coupling flange 114 and shaft opening 116.

While protective tubings, such as a lining of Tygon may be employed to prevent abrasion damage other protective means may also be used. The hub of the reel can be filled with a plastic matrix, such as foamed materials to immobilize the flow lines. Unless the flow lines on or within the spool are rigidly held, the influence of the varying centrifugal force field of the centrifuge can cause the columns to vibrate against various adjacent surfaces, particularly edges of the reel abrading the plastic tubing and causing leakage. Accordingly, in order to more rigidly secure the columns on the reel during winding it is also desirable to coat the coil with any suitable commercially available potting compound, such as a silicone or a polyurethane based material which will harden and rigidly encase the coils and secure them to the reel assembly. The outer peripheral surface of the multi-coil column can be further reinforced by covering with one or more layers of gauze cloth which is also impregnated with a potting resin.

Figure 10:
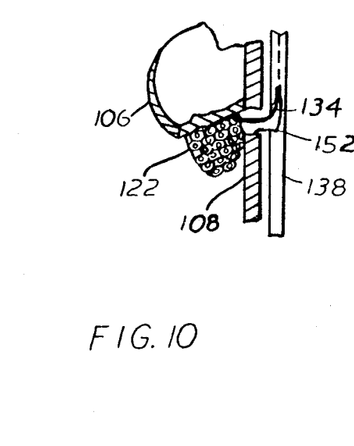
FIG. 10 is a fragmented view of a modified winding of the separation column taken along line 10—10 of FIG. 9.

FIG. 10 discloses the starting point for helically winding an odd number of radial layers of tubing, in this case separation coil 122. Instead of initiating winding adjacent to flange 102 one end begins at opening 152 in hub 108 and protective tube 138 adjacent to third reel flange 106. By initiating windings at this position the opposite end of the coil will terminate adjacent to opening 130 which permits completion of the installation pattern through protective tube 136 to exit at flange 104.

Figure 11:
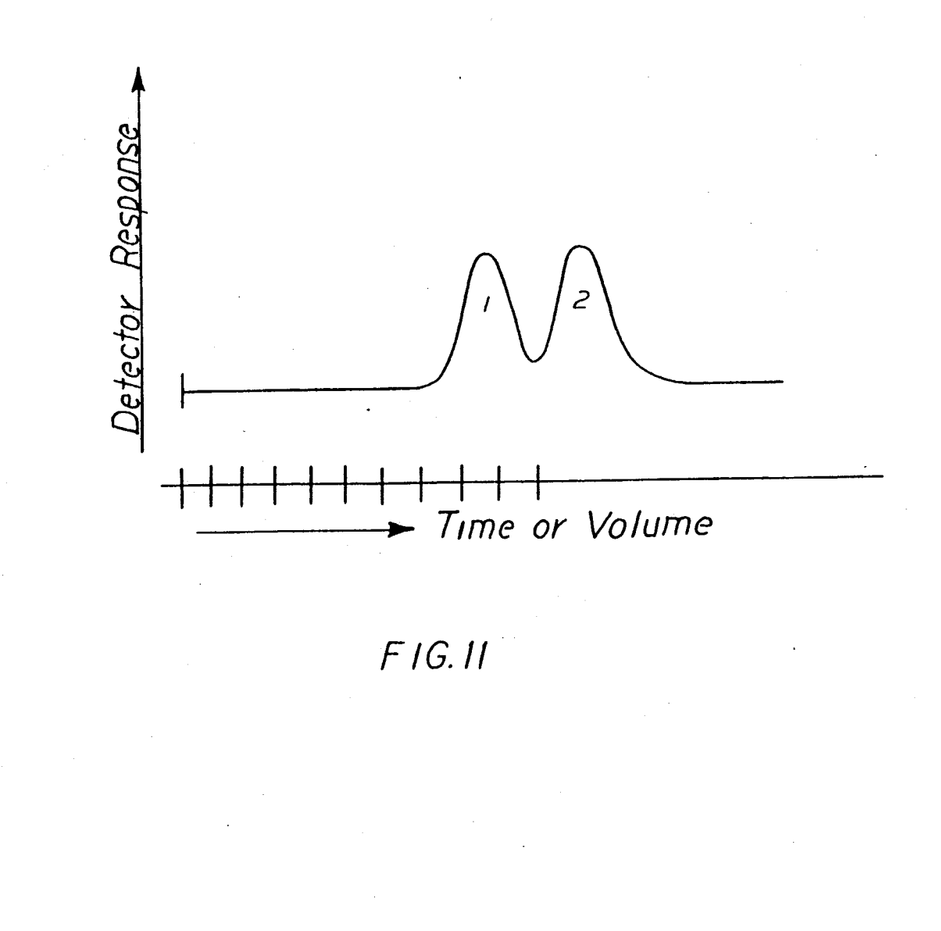
FIG. 11 is a representative chromatogram showing almost complete resolution.

As previously indicated, improved separation of the phases has been found to be substantially improved with a CCC equipped with multi-layered, multi-column separation coils when co-axially wound on a common central axis. A typical chromatogram may be represented by FIG. 11, showing almost complete resolution (separation) of the two peaks for substances 1 and 2. Several chromatographic parameters contribute to the resolution of peaks. Two of these parameters, namely "N" which is the number of theoretical plates, and "$S_F$", the fraction of column volume filled with stationary phase, are largely determined by characteristics of the chromatographic column, such as tubing size, length and coil geometry, and the conditions under which it is operated in the chromatograph, such as rpm.

$S_F$ may be measured in various ways, one of which is simply to expel the column contents following chromatography and measure the volume of each phase. A greater volume of $S_F$ will increase the distance between two peaks and thereby increase their resolution.

Figure 12:
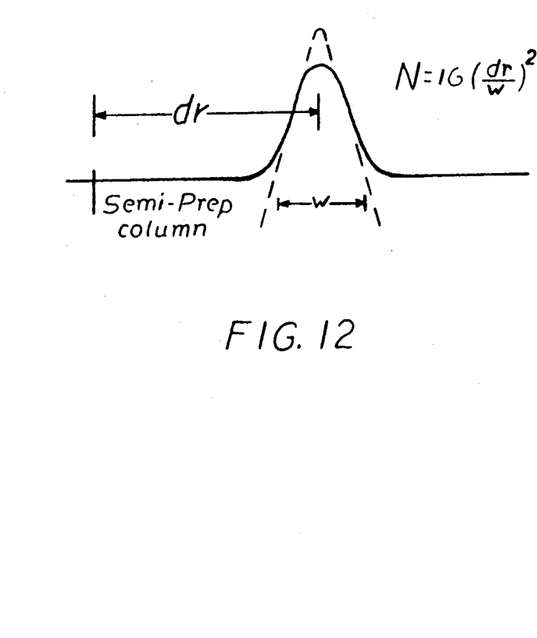
FIG. 12 is a chromatogram for calculating the number of theoretical plates.

The parameter N is actually a measure of the width of the peaks in proportion to the length of the column. It may be calculated from the chromatogram in FIG. 12 where dr represents the retention distance of the peak distance (time or volume or distance) and W represents the base width as determined by extending tangents to the peak inflection points to the baseline. W is measured in the same units as dr.

To compare columns of different length it is more convenient to use the parameter N/L where L is the column length. N/L is commonly expressed in plates/meter. Since N is known to vary with dr (dr is determined by other parameters, primarily the partition coefficient of the compound in the solvent system employed) it is desirable when comparing chromatograms employing different compounds and/or solvent systems to make the comparison with compounds of similar partition coefficient.

If the chromatographic column is improved so as to increase N/L the resulting peaks will be narrower even though dr is unchanged. Thus, a column providing a higher N/L value would allow the peaks in FIG. 11 to be resolved by making their base width, W, narrower thereby reducing or eliminating overlap of the peaks.

Accordingly, it has been found that the analytical column FIG. 9 prepared, for example, with a single layer of PTFE tubing as the analytical tubing having an i.d. of 1.07 mm and 13.7 meters long, wound at a $\beta$ (beta) value of 0.85 provided an unexpectedly high value of N/L of approximately 20. In contrast, the N/L value for measurements of the same compounds in the same solvent systems in multilayer coils in the semi-preparative and preparative range were in the range of 3 to 5.

For purposes of this invention, $\beta$ is the ratio of the distance from the reel axis to a coil layer on the spool divided by the distance from the solar axis to the reel axis. Accordingly, the present invention also contemplates CCC wherein the separation column includes an outer concentrically wound analytical tubular coil having a $\beta$ value, coil length and inside diameter sufficient to provide at least 15 plates/meter. The invention also contemplates concentrically wound analytical tubular coils wound at a $\beta$ value beginning at about 0.80 and continuing to a value of about 0.85.

While previous studies of the effect of $\beta$ on column performance may have been carried out they appear to have focused largely on $S_F$, and determined that differences in resolution are the result of changes in $S_F$. It appears that the contribution of N heretofore has not been recognized. It also appears that no studies have been performed on the effect of winding columns in a narrower range closer to 0.85. Romanach et al (J. Liq. Chromatog., 11, 91 (1988) demonstrated that columns wound over a $\beta$ range of 0.74 to 0.85 gave higher $S_F$ and thereby higher resolution than those wound over the $\beta$ range beginning at 0.5 and up to 0.85 when tubing narrower than 1.2 mm was used. According to the present invention it has been discovered that by narrowing the $\beta$ range further beginning with about 0.8 and continuing to 0.85 it appears that in addition to increased $S_F$, there is an increase in N/L bringing it in the range of 20. This represents a very significant four to five fold increase. When N/L is increased four-fold, for example, by an improvement in column construction this means the increase in resolution (separation) has been achieved without increasing the length of the column (L), and therefore, separations can be completed without an increase in time.

While the invention has been described with various embodiments, they are deemed illustrative only. Accordingly, many alternatives, modifications and variations will be apparent to persons skilled in the art in light of the foregoing detailed description, and it is therefore intended to embrace all such alternatives, modifications and variations as to fall within the spirit and broad scope of the appended claims.

I claim:

1. A coil planet centrifuge chromatographic apparatus, which comprises separation column means, support means for said separation column means, first and second spaced, parallel axes normal to the plane of said support means, said support means centrally mounted for rotation about said first axis, said separation column means eccentrically mounted on said support means for rotation about said second axis, means for revolving said support means and said separation column means around said first axis while simultaneously rotating said separation column means around said second axis, and counterweight means for balanced rotational movement of said apparatus, said separation column means comprising single reel means having a central axis and two or more separation coils adjacent to one another and helically wound around said same central axis of said single reel means to form a multi-layered coil and flow lines from said separation coils either to permit use of one of said separation coils alone, or to couple two or more separation coils in series, said coils differ from each other in either length or inside diameter.

2. The chromatographic apparatus of claim 1 wherein at least one of said separation coils of said separation column means is a preparative type.

3. The chromatographic apparatus of claim 2 wherein said separation coils of said separation column means include a preparative type and a semi-preparative type.

4. The chromatographic apparatus of claim 3 wherein said separation column means also includes an analytical type coil.

5. The chromatographic apparatus of claim 4 wherein said preparative and semi-preparative coils are multi-layered, radially wound on separate section of said reel means each being located closet to said central axis of said reel and said analytical coil comprises at least one radially wound layer wound concentrically over at least one of said preparative coils.

6. The chromatographic apparatus of claim 5 wherein said separation column includes an outer, concentrically wound analytical tubular coil having a $\beta$ value, a length and inside diameter sufficient to provide at least 15 plates/meter.

7. The chromatographic apparatus of claim 3 wherein said preparative and semi-preparative coils of said separation column means are radially wound on separate sections of the same reel means without overlapping.

8. The chromatographic apparatus of claim 1 wherein one of said separation coils of said separation column means is an analytical type.

9. The chromatographic apparatus of claim 8 wherein said separation column means also includes a preparative type coil.

10. The chromatographic apparatus of claim 9 wherein the preparative coil of said separation column means is a multi-layered radially wound tube located closest to the central axis of said reel, and said analytical coil comprises at least one radially wound layer of tubing wound concentrically over said preparative coil.

11. The chromatographic apparatus of claim 10 wherein said separation column means is located in an interior chamber and includes means for warming a dynamic solvent to and maintaining said dynamic solvent at a desired temperature prior to entry of said dynamic solvent into said separation column.

12. The chromatographic apparatus of claim 9 wherein said separation column includes an outer, concentrically wound analytical tubular coil having a $\beta$ value, length and inside diameter sufficient to provide at least 15 plates/meter.

13. The chromatographic apparatus of claim 9 wherein said preparative coils of said separation column means are connected in series.

14. The chromatographic apparatus of claim 1 where in said two or more separation coils of said separation column means are radially wound on separate sections of the same reel means without overlapping.

15. The chromatographic apparatus of claim 1 wherein said separation column includes an outer, concentrically wound analytical tubular coil having a $\beta$ value, coil length and inside diameter sufficient to provide at least 15 plates/meter.

16. The chromatographic apparatus of claim 15 wherein said analytical concentrically wound analytical tubular coil is wound on said reel means at a $\beta$ value beginning at about 0.80 and continues to a $\beta$ value of about 0.85.

17. The chromatographic apparatus of claim 1 wherein said separation coils of said separation column means are connected in series.

18. The chromatographic apparatus of claim 1 wherein said separation column means is located in an interior chamber and includes means for warming a dynamic solvent to and maintaining said dynamic solvent at a desired temperature prior to entry of said dynamic solvent into said separation column.

19. The chromatographic apparatus of claim 18 wherein said means for warming comprises a heating unit.

* * * * *